(12) United States Patent
Farber

(10) Patent No.: US 10,624,853 B1
(45) Date of Patent: Apr. 21, 2020

(54) PREPARATION OF DESICCATED LIPOSOMES FOR USE IN COMPRESSIBLE DELIVERY SYSTEMS

(71) Applicant: Smartek International Inc., Livingston, NJ (US)

(72) Inventor: Michael Farber, Livingston, NJ (US)

(*) Notice: Subject to any disclaimer, the term of this patent is extended or adjusted under 35 U.S.C. 154(b) by 0 days.

(21) Appl. No.: 16/226,734

(22) Filed: Dec. 20, 2018

Related U.S. Application Data

(63) Continuation-in-part of application No. 15/423,753, filed on Feb. 3, 2017, now Pat. No. 10,195,146.

(51) Int. Cl.
| | | |
|---|---|---|
| *A61K 36/185* | (2006.01) |
| *A61K 9/127* | (2006.01) |
| *A61K 45/06* | (2006.01) |
| *A61K 47/36* | (2006.01) |

(52) U.S. Cl.
CPC .......... *A61K 9/1277* (2013.01); *A61K 36/185* (2013.01); *A61K 45/06* (2013.01); *A61K 47/36* (2013.01)

(58) Field of Classification Search
None
See application file for complete search history.

(56) References Cited

U.S. PATENT DOCUMENTS 9,622,971 B2 * 4/2017 Farber .................. A61K 31/197

* cited by examiner

*Primary Examiner* — Celeste A Roney
(74) *Attorney, Agent, or Firm* — Michael J. Feigin, Esq.; Feigin and Fridman LLC

(57) ABSTRACT

The present document describes a compressible delivery formulation for transmucosal delivery of at least one compound which includes a micronized powder base; and a desiccated liposome formulation comprising at least one liposome containing at least one compound, process of making the same and process for making dosage forms from the formulation.

27 Claims, No Drawings

PREPARATION OF DESICCATED LIPOSOMES FOR USE IN COMPRESSIBLE DELIVERY SYSTEMS

FIELD OF THE DISCLOSED TECHNOLOGY

The subject matter disclosed generally relates to a formulation and method for delivery of an active ingredient and a process of making the same. More specifically, the subject matter disclosed relates to a formulation containing desiccated liposomes for transmucosal delivery of an active ingredient, and a process of making the same.

BACKGROUND OF THE DISCLOSED TECHNOLOGY

The technology of producing liposomes is fairly mature. Indeed, various nutritional supplements have been formulated in conjunction with liposomes to provide for improved ways of delivering effective doses of the nutritional supplements. Many nutritional supplements may be degraded when taken orally so that their delivery is not be therapeutically effective, encapsulating nutritional supplements with one or more phospholipids to form liposomes provides a measure of protection for the nutritional supplements and may enhance their therapeutic effect. Other capsule and tablet forms of protecting nutritional supplements exist, but when the capsules or tablets disintegrate in the digestive system, the nutritional supplements may not be as well received and delivered to target organs as are encapsulated liposome nutritional supplements combinations. These combinations may be in liquid or aerosol forms too depending on the best desired method of introducing such pharmaceutically active ingredients.

Furthermore, such active pharmaceutical ingredients may also enter the bodily system by passing through skin, and thus enter the systemic circulation, where in time targeted organs may benefit from yet another way of introducing active pharmaceutical ingredients. As is understood in the art skin is generally considered to be fairly impermeable to water. However, under appropriate conditions, as is understood in the art, some pharmaceutically active ingredients actually are able to penetrate the skin and enter into muscles tissues and the blood stream to relieve conditions such as arthritis and even muscle soreness due to overuse of such tissue. Appropriate exercise and appropriate foods and beverages have also been considered to be important components of maintaining good health in immune compromised individuals. Indeed, even when an individual's health is not poor, their immune system may be under attack at all times. Thus a healthy life style plus appropriate liposome nutritional supplements combinations comprising pharmaceutically active ingredients may be highly desirable to continue to remain in good overall health.

It has proven to be difficult to provide stable forms of liposome encapsulated nutritional supplements because the technology of making stable liposomes with long term stability is experimentally challenging. Often, the encapsulated nutritional supplements fall out of the liposome components and therefore are no longer encapsulated. Storage conditions must be rigorously controlled. Additionally, attempts to improve the stability of such liposome encapsulated nutritional supplement combinations have often proven to be specific to the types of nutritional supplements to be delivered and requires considerable formulating expertise.

Consequently, a need exists for improved products and methods for delivering an effective quantity of one or more nutritional supplements (or pharmaceutically active ingredients), wherein the one or more nutritional supplements reach their targeted location prior to any significant degradation. Of course, any appropriate liposome delivery pharmacokinetic method may also provide improved products and methods for targeting appropriate locations of the immune system too.

The enteral route of administration is one of the most common routes of administration for pharmaceutical compounds, and food or nutritional supplements. However, not all substances ingested through the enteral route are equally metabolized, and a lot of these substances are heavily metabolized in the gastrointestinal tract. This effect is commonly referred to the first-pass effect (also known as first-pass metabolism or presystemic metabolism). First-pass effect causes the concentration of a drug to be greatly reduced before it reaches the systemic circulation. It is the fraction of lost drug during the process of absorption which is generally related to the liver and gut wall. Notable drugs that experience a significant first-pass effect are imipramine, morphine, propranolol, buprenorphine, diazepam, midazolam, demerol, cimetidine, and lidocaine.

After a drug is swallowed, it is absorbed by the digestive system and enters the hepatic portal system. It is carried through the portal vein into the liver before it reaches the rest of the body. The liver metabolizes many drugs, sometimes to such an extent that only a small amount of active drug emerges from the liver to the rest of the circulatory system. This first pass through the liver thus greatly reduces the bioavailability of the drug. Alternative routes of administration like suppository, intravenous, intramuscular, inhalational aerosol and sublingual avoid the first-pass effect because they allow drugs to be absorbed directly into the systemic circulation.

Therefore, there is a need for formulations for the transmucosal delivery of active ingredients directly into systemic circulation. Furthermore, there is a need for processes for the preparation of formulation for the transmucosal delivery of active ingredients into the systemic circulation.

SUMMARY OF THE DISCLOSED TECHNOLOGY

1. According to an embodiment, there is provided a compressible delivery formulation for transmucosal delivery of at least one compound comprising: a micronized or milled powder base; and a desiccated liposome formulation comprising at least one liposome containing at least one compound in an amount sufficient to form a unitary dosage form containing about 10 µg to about 500 mg of the compound, depending on the molecule. The compound may be an active ingredient, a mucosal absorption enhancer, or combinations thereof. The compound may be an active ingredient, a mucosal absorption enhancer, or combinations thereof.

2. The micronized or milled powder base may be chosen from an inert powdered base, an active powdered base having improved transmucosal permeation, or combinations thereof. The inert powdered base may be chosen from a maltodextrin, a microcrystalline cellulose, lactose, sucrose, xylitol, sorbitol, mannitol, compressible gum base or combinations thereof. The active powdered base may be chosen from a caffeine, theobromine, theophylline, a plant extract with bioavailable components, creatine and/or drug base. The plant extract with bioavailable components may be chosen from a green coffee extract, guarana extract, Yerba mate extract, a tea extract, a citrus aurantium extract, or or other botanicals with nutritional or health effects. The active powdered base may be chosen from a caffeine, theobromine, creatine, and/or drug base. The caffeine may be a salt of caffeine, and the salt of caffeine may be chosen from dicaffeine malate, caffeine citrate, caffeine hydrochloride, or combinations thereof.

The formulation may further comprise a flavoring agent, and the flavoring agent may be chosen from orange flavor, lemon flavor, grapefruit flavor, blueberry flavor, raspberry flavor, strawberry flavor, peach flavor, grape flavor, apple flavor, mango flavor, banana flavor, mint flavor, cinnamon flavor, vanilla flavor, butterscotch flavor, caramel flavor chocolate flavor, and combinations thereof. The mint flavor may be chosen from spearmint flavor and peppermint flavor, and combinations thereof.

The formulation may further comprise a sweetener and the sweetener may be chosen from glucose, fructose, aspartame, cyclamate, saccharin, stevia, sucralose, brazzein, curculin, erythritol, glycyrrhizin, glycerol, hydrogenated starch hydrolysates, inulin, isomalt, lactitol, Luo han guo, mabinlin, maltitol, malto-oligosaccharide, mannitol, miraculin, monatin, monellin, osladin, pentadin, sorbitol, tagatose, thaumatin, xylitol, acesulfame potassium, alitame, salt of aspartame-acesulfame, dulcin, glucin, neohesperidin dihydrochalcone, neotame and combinations thereof.

The at least one active ingredient may be chosen from a pharmaceutical drug, a nutritional supplement, a phenylethylamine, a metabolism booster, a plant extract, an herbal medicine, an enzyme, a peptide or combinations thereof. The formulation may further comprise at least one second active ingredient. The at least one second active ingredient may be chosen from a pharmaceutical drug, a nutritional supplement, a phenylethylamine, a metabolism booster, a plant extract, an herbal medicine, an enzyme, a peptide or combinations thereof.

The pharmaceutical drug may be chosen from a nitric oxide donor, an aldosterone antagonist, an alpha-adrenergic receptor antagonist, an angiotensin II, antagonist, an angiotensin-converting enzyme inhibitor, an antidiabetic compound, an anti-hyperlipidemic compound, an antioxidant, an antithrombotic and vasodilator compound, a β-adrenergic antagonist, a calcium channel blocker, a digitalis, a diuretic, an endothelin antagonist, a hydralazine compound, a H2 receptor antagonist, a monoamine oxidase activity inhibitor, a neutral endopeptidase inhibitor, a nonsteroidal antiinflammatory compound, a phosphodiesterase inhibitor, a potassium channel blocker, a platelet reducing agent, a proton pump inhibitor, a renin inhibitor, a selective cyclooxygenase-2 inhibitor, a psychoactive drug, a stimulant, or combinations thereof. The nutritional supplement may be chosen from a vitamin, a coenzyme, a cofactor, or combinations thereof.

The phenylethylamine may be chosen from phenylethylamine, β-methylphenethylamine, β-keto-amphetamine, β-hydroxy-amphetamine, β,4-dihydroxyphenethylamine, β,4-dihydroxy-3-hydroxymethyl-N-tert-butylphenethylamine, β,3-dihydroxyphenethylamine, β,3-dihydroxy-N-methylphenethylamine, β,3,4-trihydroxyphenethylamine, β,3,4-trihydroxy-Nmethylphenethylamine, α-methylphenethylamine, α,α-dimethylphenethylamine, N-methylcathinone, N-methylamphetamine, N-methyl-β-hydroxyamphetamine, Nethylcathinone,4-methylmethcathinone, 4-hydroxyphenethylamine, 3-trifluoromethyl-N-ethyl-amphetamine, 3-trifluoromethyl-amphetamine, 3-hydroxyphenethylamine, 3-chloro-N-tert-butyl-β-ketoamphetamine, 3,4-dihydroxyphenethylamine, 3,4,5-trimethoxyphenethylamine, 2,5-dimethoxy-4-tertbutylthiophenethylamine, 2,5-dimethoxy-4-propylthiophenethylamine, 2,5-dim ethoxy-4-propylphenethylamine, 2,5-dimethoxy-4-nitrophenethylamine, 2,5-dimethoxy-4-nitroamphetamine, 2,5-dimethoxy-4-methylphenethylamine, 2,5-dimethoxy-4-methylamphetamine, 2,5-dimethoxy-4-isopropylthiophenethylamine, 2,5-dimethoxy-4-iodophenethylamine, 2,5-dimethoxy-4-iodoamphetamine, 2,5-dimethoxy-4-fluorophenethylamine, 2,5-dimethoxy-4-ethylthiophenethylamine, 2,5-dimethoxy-4-ethylphenethylamine, 2,5-dimethoxy-4-cyclopropylmethylthio-phenethylamine, 2,5-dimethoxy-4-chlorophenethylamine, 2,5-dimethoxy-4-chloroamphetamine, 2,5-dimethoxy-4-bromophenethylamine, 2,5-dimethoxy-4-bromoamphetamine, 2,5-dimethoxy-4-(2-fluoroethylthio)-phenethylamine, 2,4,5-trihydroxyphenethylamine, 3,4-methylenedioxymethcathinone, 3,4-methylenedioxy-N-methylamphetamine, N,α-butylene-β-methoxycarbonylphenethylamine, 3,4-methylenedioxy-Nethylamphetamine, 3,4-methylenedioxy amphetamine.

The phenylethylamine may be chosen from phenylethylamine, β-phenylethylamine, β-methylphenethylamine, β,4-dihydroxyphenethylamine, 3-chloro-N-tert-butyl-β-ketoamphetamine, phenelzine, and tranylcypromine.

The metabolism booster may be at least one of ephedra, an ephedra extract, ephedrine, synephrine, a Citrus aurantium extract, a Pausinystalia Yohimbe extract, and yohimbine, epigallocatechin gallate, or oleoylethanolamide. The monoamine oxidase activity inhibitor may be at least one of Piperine, methyl piperate, a piperine derivative, a methyl piperate derivative, St. John's Wort, American Ginseng, Asian Ginseng, 5-hydroxy tryptophan, Bitter Orange, Brewer's Yeast, Vitamin B6, L-Tyrosine and Yohimbe.

The formulation may be further comprising a mucosal absorption enhancer for improved transmucosal permeation. The mucosal absorption enhancer may comprise at least one of 23-lauryl ether, aprotinin, azone, benzalkonium chloride, cetylpyridinium chloride, cetyltrimethylammonium bromide, cyclodextrin, dextran sulfate, lauric acid, lauric acid/ Propylene glycol, lysophosphatidylcholine, menthol, methoxysalicylate, methyloleate, oleic acid, piperine, phosphatidylcholine, polyoxyethylene, polysorbate 80, sodium EDTA, sodium glycocholate, sodium glycodeoxycholate, sodium lauryl sulfate, sodium salicylate, sodium taurocholate, sodium taurodeoxycholate, sodium deoxycholate, a sulfoxide, bile salts, and an alkyl glycoside. According to another embodiment, there is provided a dosage form for transmucosal delivery of at least one compound comprising: a formulation of the present invention in combination with a pharmaceutically acceptable carrier.

The dosage form may be chosen from a chewable tablet, a fast disintegrating tablet, a chewing gum, a granule, and a suppository. The dosage form may be chosen from a jelly, a gel, a film, a lozenge, a toothpaste, an ointment.

The pharmaceutically acceptable carrier may be a hydrocolloid, and the hydrocolloid may be chosen from agar, agarose, alginates, carrageenan (iota, kappa, lambda), cellulosics, chitosan, gelatin, gellan gum, guar gum, gum arabic, locust bean gum, pectin, soybean gel, starch, whey protein, xanthan gum, chewing gum, a base gum and derivatives thereof and combinations thereof. According to another embodiment, there is provided a process for the preparation of a solid dosage form comprising: a) compressing a formulation of the present invention in combination with a pharmaceutically acceptable carrier, without a heat treatment capable of causing degradation of the formulation.

According to another embodiment, there is provided a process for the preparation of a formulation for transmucosal delivery of at least one compound comprising: a) spraying a liposome formulation suspended in a water based solvent on a micronized powder base, the liposome formulation comprising at least one liposome containing at least one compound in an amount sufficient to form a unitary dosage form containing from 10 μg to about 500 mg of the compound, at a temperature at a nozzle head aperture of about 60° C. or less to evaporate some or most of the water based solvent and desiccate the liposome wherein the liposome formulation comprises the compound. For purposes of this disclosure, "spraying" is defined as "applying (liquid) to someone or something in the form of a shower of drops." The drop size in spraying is between 0.005 mm to 2 mm in diameter in embodiments of the disclosed technology. In other embodiments, the drop size can be up to 10 mm diameter.

The compound may be an active ingredient, a mucosal absorption enhancer, or combinations thereof. The micronized powder base may be chosen from an inert powdered base, an active powdered base having improved transmucosal permeation, or combinations thereof. The inert powdered base may be chosen from a maltodextrin, a microcrystalline cellulose, sucrose, xylitol, sorbitol, mannitol, or combinations thereof. The active powdered base may be chosen from a caffeine, theobromine, theophylline, a plant extract with bioavailable components, and creatine. The plant extract with bioavailable components may be chosen from a green coffee extract, guarana extract, Yerba mate extract, a tea extract, a citrus aurantium extract, or combinations thereof. The active powdered base may be chosen from a caffeine, theobromine, and creatine. The caffeine may be a salt of caffeine. The salt of caffeine may be chosen from dicaffeine malate, caffeine citrate, caffeine hydrochloride, or combinations thereof. soluble active.

The water based solvent may further comprise a flavoring agent and the flavoring agent may be chosen from orange flavor, lemon flavor, grapefruit flavor, blueberry flavor, raspberry flavor, strawberry flavor, peach flavor, grape flavor, apple flavor, mango flavor, banana flavor, mint flavor, cinnamon flavor, vanilla flavor, butterscotch flavor, caramel flavor chocolate flavor, and combinations thereof. The water based solvent may further comprise a sweetener, and the sweetener may be chosen from glucose, fructose, aspartame, cyclamate, saccharin, stevia, sucralose, brazzein, curculin, erythritol, glycyrrhizin, glycerol, hydrogenated starch hydrolysates, inulin, isomalt, lactitol, Luo han guo, mabinlin, maltitol, malto-oligosaccharide, mannitol, miraculin, monatin, monellin, osladin, pentadin, sorbitol, tagatose, thaumatin, xylitol, acesulfame potassium, alitame, salt of aspartame-acesulfame, dulcin, glucin, neohesperidin dihydrochalcone, neotame and combinations thereof. The water based solvent may be a mixture of water and alcohol and the alcohol may be ethanol.

The at least one active ingredient may be chosen from a pharmaceutical drug, a nutritional supplement, a phenylethylamine, a metabolism booster, a plant extract, an herbal medicine, an enzyme, a peptide or combinations thereof.

The process may further comprise at least one second active ingredient. The at least one second active ingredient may be chosen from a pharmaceutical drug, a nutritional supplement, a phenylethylamine, a metabolism booster, a plant extract, an herbal medicine, an enzyme, a peptide or combinations thereof.

The pharmaceutical drug may be chosen from a nitric oxide donor, an aldosterone antagonist, an alpha-adrenergic receptor antagonist, an angiotensin II, antagonist, an angiotensin-converting enzyme inhibitor, an antidiabetic compound, an anti-hyperlipidemic compound, an antioxidant, an antithrombotic and vasodilator compound, a β-adrenergic antagonist, a calcium channel blocker, a digitalis, a diuretic, an endothelin antagonist, a hydralazine compound, a H2 receptor antagonist, a monoamine oxidase activity inhibitor, a neutral endopeptidase inhibitor, a nonsteroidal antiinflammatory compound, a phosphodiesterase inhibitor, a potassium channel blocker, a platelet reducing agent, a proton pump inhibitor, a renin inhibitor, a selective cyclooxygenase-2 inhibitor, a psychoactive drug, a stimulant, or combinations thereof. The nutritional supplement may be chosen from a vitamin, a coenzyme, a cofactor, or combinations thereof.

The phenylethylamine may be chosen from phenylethylamine, β-methylphenethylamine, β-keto-amphetamine, β-hydroxy-amphetamine, β,4-dihydroxyphenethylamine, β,4-dihydroxy-3-hydroxymethyl-N-tertbutylphenethylamine, β,3-dihydroxyphenethylamine, β,3-dihydroxy-Nmethylphenethylamine, β,3,4-trihydroxyphenethylamine, β,3,4-trihydroxy-Nmethylphenethylamine, α-methylphenethylamine, α,α-dimethylphenethylamine, N-methylcathinone, N-methylamphetamine, N-methyl-β-hydroxyamphetamine, Nethylcathinone, 4-methylmethcathinone, 4-hydroxyphenethylamine, 3-trifluoromethyl-N-ethyl-amphetamine, 3-trifluoromethyl-amphetamine, 3-hydroxyphenethylamine, 3-chloro-N-tert-butyl-β-ketoamphetamine, 3,4-dihydroxyphenethylamine, 3,4,5-trimethoxyphenethylamine, 2,5-dimethoxy-4 tertbutylthiophenethylamine, 2,5-dimethoxy-4-propylthiophenethylamine, 2,5-dimethoxy-4-propylphenethylamine, 2,5-dimethoxy-4-nitrophenethylamine, 2,5-dimethoxy-4-nitroamphetamine, 2,5-dimethoxy-4-methylphenethylamine, 2,5-dimethoxy-4-methylamphetamine, 2,5-dimethoxy-4-isopropylthiophenethylamine, 2,5-dimethoxy-4-iodophenethylamine, 2,5-dimethoxy-4-iodoamphetamine, 2,5 dimethoxy-4-fluorophenethylamine, 2,5-dimethoxy-4-ethylthiophenethylamine, 2,5-dimethoxy-4-ethylphenethylamine, 2,5-dimethoxy-4-cyclopropylmethylthio-phenethylamine, 2,5-dimethoxy-4-chlorophenethylamine, 2,5-dimethoxy-4 chloroamphetamine, 2,5-dimethoxy-4-bromophenethylamine, 2,5-dimethoxy-4-bromoamphetamine, 2,5-dimethoxy-4-(2-fluoroethylthio)-phenethylamine, 2,4,5-trihydroxyphenethylamine, 3,4-methylenedioxymethcathinone, 3,4-methylenedioxy-N-methylamphetamine, N,α-butylene-β methoxycarbonylphenethylamine, 3,4-methylenedioxy-Nethylamphetamine, 3,4-methylenedioxyamphetamine.

The phenylethylamine may be chosen from phenylethylamine, β-phenylethylamine, β-methylphenethylamine, β,4-dihydroxyphenethylamine, 3-chloro-N-tert-butyl-β-ketoamphetamine, phenelzine, and tranylcypromine. The monoamine oxidase activity inhibitor may be at least one of Piperine, methyl piperate, pepper extracts, a piperine derivative, a methyl piperate derivative, St. John's Wort, American Ginseng, Asian Ginseng, 5-hydroxy tryptophan, Bitter Orange, Brewer's Yeast, Vitamin B6, L-Tyrosine and Yohimbe. The metabolism booster may be at least one of ephedra, an ephedra extract, ephedrine, synephrine, a Citrus aurantium extract, a Pausinystalia Yohimbe extract, and yohimbine. The process may further comprise a mucosal absorption enhancer for improved transmucosal permeation.

The mucosal absorption enhancer may comprise at least one of 23-lauryl ether, aprotinin, azone, benzalkonium chloride, cetylpyridinium chloride, cetyltrimethylammonium bromide, cyclodextrin, dextran sulfate, lauric acid, lauric acid/Propylene glycol, lysophosphatidylcholine, menthol, methoxysalicylate, methyloleate, oleic acid, piperine, methyl piperate, pepper extracts phosphatidylcholine, polyoxyethylene, polysorbate 80, sodium EDTA, sodium glycocholate, sodium glycodeoxycholate, sodium lauryl sulfate, sodium salicylate, sodium taurocholate, sodium taurodeoxycholate, sodium deoxycholate, a sulfoxide, bile salts, and an alkyl glycoside.

According to another embodiment, there is provided a compressible delivery formulation for transmucosal delivery of at least one active ingredient prepared by the process of the present invention. According to another embodiment, there is provided a solid dosage form prepared by compressing a formulation of the present invention, without a heat treatment capable of causing degradation of the formulation.

The following terms are hereinafter defined. The term "micronized" or "micronization" are intended to mean the process of reducing the average diameter of a solid material's particles to produce particles that are only a few micrometers in diameter.

The term "liposome" is intended to mean an artificially-prepared vesicle composed of a lipid bilayer. The liposome can be used as a vehicle for administration of nutrients and pharmaceutical drugs, and it can be prepared by disrupting biological membranes (such as by sonication). Liposomes are composed of natural phospholipids, and may also contain mixed lipid chains with surfactant properties (e.g., egg phosphatidylethanolamine). The major types of liposomes are the multilamellar vesicle (MLV), the small unilamellar vesicle (SUV), and the large unilamellar vesicle (LUV).

It should be understood that the use of "and/or" is defined inclusively such that the term "a and/or b" should be read to include the sets: "a and b," "a or b," "a," "b." Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

DETAILED DESCRIPTION OF EMBODIMENTS OF THE DISCLOSED TECHNOLOGY

In a first embodiment, there is disclosed a compressible delivery formulation for transmucosal delivery of at least one compound comprising: a micronized powder base; a dessicated liposome formulation comprising at least one liposome containing at least one compound. In a second embodiment, there is disclosed a dosage form for transmucosal delivery of at least one compound comprising a formulation of the present invention in combination with a pharmaceutically acceptable carrier, and the dosage form may contain from about 10 µg to about 500 mg of the compound. In a third embodiment, there is disclosed a process for the preparation of solid dosage form by compressing a formulation of the present invention in combination with a pharmaceutically acceptable carrier, without a heat treatment capable of causing degradation of the formulation.

In a fourth embodiment, there is disclosed a process for the preparation of a formulation for transmucosal delivery of at least one compound comprising spraying a liposome formulation suspended in a water based solvent on a micronized powder base. The liposome formulation comprises at least one liposome containing at least one compound. The spraying is effected at a temperature at a nozzle head aperture of about 30 C to 50° C. or less, to desiccate the liposomes. In a fifth embodiment, there is disclosed a formulation for transmucosal delivery of at least one compound prepared by the process of the present invention. In a sixth embodiment, there is disclosed a solid dosage form prepared by compressing a formulation of the present invention, without a heat treatment capable of causing degradation of the formulation.

According to the first embodiment, there is disclosed a formulation for transmucosal delivery of at least one compound comprising: a micronized powder base; a desiccated liposome formulation comprising at least one liposome containing at least one compound. According to an embodiment, the dessicated liposome formulation comprises the compound in an amount sufficient to form a unitary dosage form containing from about 10 µg to about 500 mg of the compound. The compound may be an active ingredient, a mucosal absorption enhancer, or combinations thereof.

According to an embodiment, the micronized powder base may be an inert powdered base, an active powdered base having improved transmucosal permeation, or combinations thereof. Examples of inert powdered base include without limitations maltodextrins, microcrystalline cellulose, sucrose, xylitol, sorbitol, and mannitol. As used herein, the term inert is intended to mean that the powdered base does not illicit any therapeutic physiological effect in organism consuming the formulation.

Maltodextrins are polysaccharides that are used as a food additive. They are produced from starch by partial hydrolysis and are usually found as a white hygroscopic spray dried powders. Maltodextrins are easily digestible, being absorbed as rapidly as glucose, and might be either moderately sweet or almost flavorless. They are commonly used for the production of sodas and candy and can also be found as an ingredient in a variety of other processed foods.

Microcrystalline cellulose is a term for refined wood pulp and is used as a texturizer, an anti-caking agent, a fat substitute, an emulsifier, an extender, and a bulking agent in food production. The most common form is used in vitamin supplements or tablets. Sucrose is the organic compound commonly known as table sugar and sometimes called saccharose. A white, odorless, crystalline powder with a sweet taste, it is best known for its nutritional role. Xylitol, sorbitol, and mannitol are sugar alcohol sweetener used as a naturally occurring sugar substitute.

As used herein, the term "active" is intended to mean that the powdered base does have a therapeutic physiological effect in organism consuming the formulation. Non limiting examples of active powdered base are caffeine, theobromine, theophylline, a plant extract with bioavailable components, and creatine. Examples of plant extract with bioavailable components include green coffee extract, guarana extracts, Yerba mate extracts, tea extract, citrus aurantium extracts, and combinations thereof. Preferred active powdered base are include caffeine, theobromine, and creatine. Preferably, the caffeine is a salt of caffeine, such as for example dicaffeine malate, caffeine citrate, caffeine hydrochloride, or combinations thereof.

According to another embodiment, the formulation of the present invention may comprise dessicated liposome formulation that comprising at least one liposome containing at least one compound. The liposome formulation may contain more than one type of liposome, each of which may be loaded with one or more different compound. According to an embodiment, the liposome(s) are loaded with the compound(s) with sufficient amounts of compounds to achieve unitary doses (dosage forms) capable of delivering from about 10 µg to about 500 mg of the compound(s), or from about 100 µg to about 500 mg, or from about 200 µg to about 500 mg, or from about 300 µg to about 500 mg, or from about 400 µg to about 500 mg, or from about 500 µg to about 500 mg, or from about 600 µg to about 500 mg, or from about 700 µg to about 500 mg, or from about 800 µg to about 500 mg, or from about 900 µg to about 500 mg, or from about 1 mg to about 500 mg, or from about 10 mg to about 500 mg, or from about 10 mg to about 400 mg, or from about 10 mg to about 300 mg, or from about 10 mg to about 200 mg, or from about 10 mg to about 100 mg, or from about 10 mg to about 50 mg, or from about 10 mg to about 25 mg, or from about 25 mg to about 500 mg, or from about 25 mg to about 400 mg, or from about 25 mg to about 300 mg, or from about 25 mg to about 200 mg, or from about 25 mg to about 100 mg, or from about 25 mg to about 50 mg, or from about 50 mg to about 500 mg, or from about 50 mg to about 400 mg, or from about 50 mg to about 300 mg, or from about 50 mg to about 200 mg, or from about 50 mg to about 100 mg, or from about 100 mg to about 500 mg, or from about 100 mg to about 400 mg, or from about 100 mg to about 300 mg, or from about 100 mg to about 200 mg, or from about 200 mg to about 500 mg, or from about 200 mg to about 400 mg, or from about 200 mg to about 300 mg, or from about 300 mg to about 500 mg, or from about 300 mg to about 400 mg, or from about 400 mg to about 500 mg. Without wishing to be bound by theory, the amount of compound will vary according to the compound selected, and the desired dosage required to obtain the desired health beneficial effect or therapeutic effect. The person skilled in the art is capable of determining the amount of compound necessary to be loaded into the liposomes in order to achieve the desired amounts in the final dosage forms.

The use of desiccated liposomes in the formulation of the present invention allows for the preparation of formulations having low water content that have long shelf life. Furthermore, upon contact with the bodily fluids in the body cavity in proximity to the target mucosa (e.g. buccal, vaginal or anal), the desiccated liposomes present in the formulation of the present invention rehydrate and the liposomes are shown under microscope to be normal sphericals (i.e filled with water) to provide one or more liposome encapsulated compounds in situ. Without wishing to be bound by theory, it is believed that upon contact with the mucosa, the content of the liposome is delivered transmucosally directly into the systemic circulation. Furthermore, the use of desiccated liposomes also contributes to masking of the taste of some of the compounds that they contain, thereby helping to provide a more palatable delivery system.

According to an embodiment, unilamellar liposomes may be used to contain water soluble compounds for higher bioavailability and faster absorption. For example, such liposomes could be used to encapsulate phenylethylamine salts. According to another embodiment, bilamellar (i.e. multilamellar) liposomes may also be used for lipid soluble compounds such as lipid soluble flavones, ecdysterones, or coenzyme Q10, along with water soluble compounds in the hydrophilic core. These lipid soluble compounds may be first dissolved in suitable lipid solvents such as extra virgin olive oil and then incorporated into the liposomes.

According to another embodiment, the formulation of the present invention may further comprise flavoring and sweetening agents. The flavoring and sweetening agents further improve the palatability and mouth feel of the formulation of the present invention. For example, the flavoring agent may be chosen from orange flavor, lemon flavor, grapefruit flavor, blueberry flavor, raspberry flavor, strawberry flavor, peach flavor, grape flavor, apple flavor, mango flavor, banana flavor, mint flavor, cinnamon flavor, vanilla flavor, butterscotch flavor, caramel flavor chocolate flavor, and combinations thereof. Preferably, the flavoring may be a mint flavor. Most preferably, the flavoring may be chosen from spearmint flavor and peppermint flavor, and combinations thereof.

Examples of sweeteners include but are not limited to glucose, fructose, aspartame, cyclamate, saccharin, stevia, sucralose, brazzein, curculin, erythritol, glycyrrhizin, glycerol, hydrogenated starch hydrolysates, inulin, isomalt, lactitol, Luo han guo, mabinlin, maltitol, malto-oligosaccharide, mannitol, miraculin, monatin, monellin, osladin, pentadin, sorbitol, tagatose, thaumatin, xylitol, acesulfame potassium, alitame, salt of aspartame-acesulfame, dulcin, glucin, neohesperidin dihydrochalcone, neotame and combinations thereof.

According to another embodiment, the formulation of the present invention may further comprise a mucosal absorption enhancer for improved transmucosal permeation. According to an embodiment, the mucosal absorption enhancer may be one of the compounds included in one of the liposome formulation used in the present invention. According to another embodiment, the mucosal absorption enhancer may be added as a further ingredient of the formulation of the present invention, without the benefit of liposome encapsulation.

Limited examples of mucosal absorption enhancer include but are not to 23-lauryl ether, aprotinin, azone, benzalkonium chloride, cetylpyridinium chloride, cetyltrimethylammonium bromide, cyclodextrin, dextran sulfate, lauric acid, lauric acid/Propylene glycol, lysophosphatidylcholine, menthol methoxysalicylate, methyloleate, oleic acid, piperine, phosphatidylcholine, polyoxyethylene, polysorbate 80, sodium EDTA, sodium glycocholate, sodium glycodeoxycholate, sodium lauryl sulfate, sodium salicylate, sodium taurocholate, sodium taurodeoxycholate, sodium deoxycholate, a sulfoxide, bile salts, and an alkyl glycoside. Preferably, the mucosal absorption enhancer is piperine. Most preferably, the mucosal absorption enhancer is liposome encapsulated piperine. Most preferable, liposome encapsulated piperine is used in about 100 µg to about 200 µg per dosage form.

According to another embodiment, the desiccated liposomes may be loaded with an active ingredient. According to another embodiment, an active ingredient may also be added to the formulation of the present invention without the benefit of liposomal encapsulation. According to an embodiment, the active ingredient may have good bioavailability after first-pass metabolism. However, the formulation of the present invention accelerates the rate at which the active ingredient reaches systemic circulation over enteral administration.

According to another embodiment, the active ingredient is an active ingredient having a low bioavailability. In such as case, it is believed that the formulation of the present invention may accelerate the rate at which the active ingredient reaches systemic circulation over enteral administration, and increase the amount of the active ingredient which is bioavailable over enteral administration. Examples of compounds having low bioavailability include but are not limited to coenzyme Q10, glutathione, steroids, sterols, saponins, synephrine, resveratrol, quercitin, oleoylethanolamide, etc.

The active ingredient may be any one of a pharmaceutical drug, a nutritional supplement, a plant extract, an herbal medicine, an enzyme, a peptide or combinations thereof.

Non limiting examples of pharmaceutical drugs include nitric oxide aldosterone antagonists, alpha-adrenergic receptor antagonists, angiotensin II, antagonists, angiotensin-converting enzyme inhibitors, antidiabetic compounds, anti-hyperlipidemic compounds, antioxidants, antithrombotic and vasodilator compounds, β-adrenergic antagonists, calcium channel blockers, digitalis, diuretic, endothelin antagonists, hydralazine compounds, H2 receptor antagonists, neutral endopeptidase inhibitors, nonsteroidal antiinflammatory compounds, phosphodiesterase inhibitors, potassium channel blockers, platelet reducing agents, proton pump inhibitors, renin inhibitors, selective cyclooxygenase-2 inhibitors, psychoactive drugs, stimulants, or combinations thereof. Non limiting examples of nutritional supplements include vitamins, coenzymes, cofactors, or combinations thereof.

According to the second embodiment, the formulations of the present inventions may be included into dosage forms, along with suitable pharmaceutically acceptable carriers, and the dosage form contains from about 10 µg to about 500 mg of the compound. Examples of suitable dosage forms for transmucosal delivery include but are not limited to chewable tablets, fast disintegrating tablets, jellies, gels, chewing gum, granules, films, lozenges, toothpastes and liquids (e.g. mouthwashes), which may be administered buccally (i.e. through the buccal mucosa), as well as ointments, and suppositories, which may be administered through the vaginal and anal mucosa. Preferred dosage forms are chosen from chewable tablets, fast disintegrating tablets, chewing gums, granules, and suppositories. Other suitable dosage forms include a jelly, a gel, a film, a lozenge, a toothpaste, an ointment.

According to an embodiment, the dosage form of the present invention may contain any suitable pharmaceutically acceptable carriers as known in the art. According to an embodiment, a preferred pharmaceutically acceptable carrier is a hydrocolloid. As used herein, hydrocolloids are substances that form a gel in the presence of water. Examples of hydrocolloids include but are not limited to agar, agarose, alginates, carrageenan (iota, kappa, lambda), cellulosics, chitosan, gelatin, gellan gum, guar gum, gum arabic, locust bean gum, pectin, soybean gel, starch, whey protein, xanthan gum, chewing gum, a base gum and derivatives thereof and combinations thereof.

According to another embodiment, there is disclosed a process for the preparation of a formulation for transmucosal delivery of at least one active ingredient by spraying a liposome formulation suspended in a water based solvent on a micronized powder base (as described above). The liposome formulation comprises at least one liposome containing at least one compound (as described above). Spraying is effected preferably in a fluidized bed, or any suitable apparatus. Spraying is effected at a temperature at a nozzle head aperture of about 30° C. to 50° C. or less. Spraying of the liposome formulation in this fashion causes the water based solvent to evaporate and/or be absorbed by the anhydrous micronized base, as well as dissipate the heat present in the water based solvent, and results in desiccation of the liposome without damaging them.

According to an embodiment, about 0.2 L to about 0.4 L of the liposome formulation suspended in a water based solvent is sprayed for each 1 kg of the micronized powder base. Therefore, the volume of liposome formulation suspended in a water based solvent sprayed for each 1 kg of the micronized powder base may be from about 0.1 L to about 0.5 L, or from about 0.4 L to about 0.6 L, or from about 0.4 L to about 0.7 L, or from about 0.4 L to about 0.8 L, or from about 0.4 L to about 0.9 L, or from about 0.4 L to about 1.0 L, or from about 0.5 L to about 0.6 L, or from about 0.5 L to about 0.7 L, or from about 0.5 L to about 0.8 L, or from about 0.5 L to about 0.9 L, or from about 0.5 L to about 1.0 L, or from about 0.6 L to about 0.7 L, or from about 0.6 L to about 0.8 L, or from about 0.6 L to about 0.9 L, or from about 0.6 L to about 1.0 L, or from about 0.7 L to about 0.8 L, or from about 0.7 L to about 0.9 L, or from about 0.7 L to about 1.0 L, or from about 0.8 L to about 0.9 L, or from about 0.8 L to about 1.0 L, or from about 0.9 L to about 1.0 L. When the volume is from about 0.2 L to about 0.5 L for each 1 kg of the micronized powder base, the desiccation of the liposome occurs without substantial disruption of the liposomal membrane (where "substantial disruption" is defined as no less than 80% of the membranes remain intact).

According to an embodiment, the liposome formulation comprises the compound in an amount sufficient to form unitary dosage forms that contain from about 10 µg to about 500 mg of compound. Without wishing to be bound by theory, the amount of compound will vary according to the compound selected, and the desired dosage required to obtain the desired health beneficial effect or therapeutic effect. The person skilled in the art is capable of determining the amount of compound necessary to be loaded into the liposomes in order to achieve the desired amounts in the final dosage forms.

According to an embodiment, the water based solvent may be water, or a mixture of water and alcohol. For example, the alcohol may be ethanol. According to another embodiment, the water based solvent may further comprise flavoring agents, sweetening agent, or combinations thereof. According to another embodiment, the water based solvent may further comprise second active ingredients, mucosal absorption enhancer, or combinations thereof. Alternatively, according to another embodiment, the second active ingredients, mucosal absorption enhancer, or combinations thereof may be included with the micronized powder base, and sprayed with the liposome formulations.

According to another embodiment, there is provided a process for the preparation of a solid dosage form by compressing a formulation of the present invention as described above, in combination with a pharmaceutically acceptable carrier as described above, without a heat treatment capable of causing degradation of the formulation. As used herein, without a heat treatment capable of causing degradation of the formulation is intended to mean that only compression is used during the preparation of the dosage form. No heat treatment that would damage the liposome present in the formulation of the present invention should be used. Liposomes are notoriously sensitive to increased temperatures that damage the phospholipids constituting their bilayers; and hence temperature should be kept as low as possible and not exceeding 50° C. when preparing the dosage form from the formulation of the present invention.

The present invention will be more readily understood by referring to the following example which is given to illustrate the invention rather than to limit its scope. EXAMPLE 1: 7-methoxyflavone formulation. 7-methoxyflavone has poor bioavailability of approximately 5%. Liposome containing 7-methoxyflavone are formed with 7-methoxyflavone first dissolved in extra virgin olive oil along with piperine, and the mixture is sprayed onto microcrystalline cellulose or maltodextrin in a fluid bed. The resulting powder is mixed with additional bulking agents and compressed into tablets.

In some embodiments of the disclosed technology, a process for preparation of a formulation for transmucosal delivery is carried out as follows. A phospholipid complex with a liposome is applied to a formulation suspended in a water based solvent to a dried substrate. That is, the phospholipid complex is "wet" (has a liquid quality thereof). This step is carried out below the glass transition temperature of the phospholipid complex. The glass transition temperature is defined as a temperature where a polymer melt changes on cooling to a polymer glass or a polymer glass changes on heating to a polymer. The phsopholipid complex is defined as a chemical or drug that is attached to a lipid (fat) that has phosphorus. After the application of the wet formulation, such as by spraying on the dried substrate, the formulation is dried in heat which is at or less than 60 degrees, at or less than 45 degrees, or at room temperature (25 degrees; all degree measurements are in Celsius). The drying is continued until the moisture or measure of wetness (percent liquid) is at or below 5% and/or at or below 3%.

In the above embodiment, the substrate previously hydrated can be primarily (at least 50% by weight) a hydrocolloid such as one or both of pullulan or carrageen. The formulation being applied to the dried substrate is added thereto or applied to the dried substrate while simultaneously mixing and pouring. The result, in some embodiments, is the formation of a thin film of the formulation on the dry substrate. "Thin" for purposes of this disclosure is defined as between 100 and 500 microns wide. Multiple such thin film layers can be added such as by allowing a first layer to dry then adding a second layer, a third layer, and so forth. The desiccated liposomes are powdered in some embodiments of the disclosed technology and adhere to the thin film due to a static charge which has been given or imparted on the liposomes. The static charge can be applied before or after the liposomes have been added to the formulation, depending on the embodiment thereof.

The formulation can have additional components such as additives. Such additives can be the one or more of adding flavor, plasticizing, adding color, adding sweetness, adding thickening, adding preservation, and adding bitterness blocking. That is, the additives, in embodiments of the disclosed technology, may be for changing the taste, consistency, or longevity of the resulting medicinal compound to be ingested.

The mass of said liposome with actives (active ingredients—those ingredients which have an intended medicinal effect within a human body) is from 5% to 45% of tge titak dry mass of the formulation, in some embodiments of the disclosed technology. The active ingredient can be a cannabinoid or others described with reference to other embodiments of the disclosed technology, above.

The lipids in the formulation can be at a concentration which at or about above 150 millimoles and/or 200 millimoles. The formulation, in some such embodiments, lacks a sugar stabilizer but can have an additive which aids in absorption of the liposome across a mucosal membrane. Such an additive can be a mucosal absorption enhancer, which is described in more detail above. The additive (mucosal absorption enhancer) can be lipophilic or hydrophilic and in some embodiments are incorporated into an oil phase of the liposome such as where the additive is lipophilic. Or the additives are added to the liquid phase after formation of the liposomes. In yet another alternative, when using a liposomal desiccated powder, the additive is added to a granulated (also referred to as powdered) dessicated liposome.

A compound to be encapsulated in a hydrophilic core of the liposomes is also used in embodiments of the disclosed technology. This compound can be a pharmaceutical drug or drugs (defined as "a chemical compound with known and intended medicinal effect in the body), a glycoside, an inclusion complex with cyclodextrin, a cannabinoid, a derivatives of a cannabinoid, a nanocomplexed cyclodextrin with lipids, a nutraceutical compound (a food containing health-giving additives and having medicinal benefit), salts of nutraceutical components, or the like.

The liposomes, in some embodiments, comprise from 0.01 to 0.1% Polysorbate 80 or Polysorbate 20 as stabilizers. Polysorbate 80 is the common name for Polyoxyethylene (20) sorbitan monooleate, and polysorbate 20 is the common name for Polyoxyethylene (20) sorbitan monolaurate.

The liposomal fluid is formed by first forming an oil based fluid to dissolve lipophilic actives and lipophilic penetration enhancers in some embodiments. In such embodiments the lipophilic actives are selected from one of pharmaceutical drugs, cannabinoids, terpenes, or nutraceutucals. The oil based fluid is added to a water based fluid and stirred at between approximately 500 and 2000 rpm modifying a surface tension so that large multilamellar liposomes are formed. The phospholipids are chosen from natural or synthetic phospholipids in embodiments. The desiccated liposomes are formulated into one of a chewable gum, lozenge, wafer, granule, and thin orodispersible films in some embodiments of the disclosed technology.

While the disclosed technology has been taught with specific reference to the above embodiments, a person having ordinary skill in the art will recognize that changes can be made in form and detail without departing from the spirit and the scope of the disclosed technology. The described embodiments are to be considered in all respects only as illustrative and not restrictive. All changes that come within the meaning and range of equivalency of the claims are to be embraced within their scope. Combinations of any of the methods and apparatuses described hereinabove or similar apparatuses that can be used for uniform application of the liposomal formulation onto the micronized base are also contemplated and within the scope of the invention. It should be further understood that the term "about" is defined to be within a standard tolerance level known in the art, or if such a definition is considered imprecise, then within 5% of the amount for which "about" is modifying. All terms listed with the modifier "about" may also be claimed and considered to be disclosed in the exact amount specified.

I claim:

1. A process for the preparation of a formulation for transmucosal delivery of at least one encapsulated active compound comprising:

at a temperature less than a glass transition temperature of a phospholipid complex with a liposome being applied, adding said liposome in a formulation suspended in a water based solvent to a dried substrate;

drying in heat less than 60 degrees Celsius until moisture of said liposome formulation is less than or equal to 5%.

2. The process of claim 1, wherein said substrate is previously hydrated with a hydrocolloid.

3. The process of claim 2 wherein said hydrocolloid is at least one of pullulan and carrageen.

4. The process of claim 2, wherein said adding is simultaneous to mixing and pouring causing a thin film of said formulation to form onto a solid surface due to said pouring.

5. The process of claim 4, wherein said adding comprises multiple said thin film layers.

6. The process of claim 4, further comprising a step of adding a static charge to powdered desiccated liposomes and adhering said powdered desiccated liposomes to said thin film.

7. The process of claim 1, wherein said formulation comprises at least one additive for purposes of at least two of: adding flavor, plasticizing, adding color, adding sweetness, adding thickening, adding preservation, and adding bitterness blocking.

8. The process of claim 1, wherein mass of said liposome with actives is about from 5% to 45% of dry mass of said formulation.

9. The process of claim 8, wherein an active ingredient in said formulation is a cannabinoid.

10. The process of claim 1, wherein a concentration of lipids in said formulation is above 150 millimoles.

11. The process of claim 1, wherein a concentration of lipids in said formulation is above 200 millimoles.

12. The process of claim 6, wherein said formulation is without a sugar stabilizer.

13. The process of claim 12, wherein said formulation comprises additives which aid in absorption of said liposome across a mucosal membrane.

14. The process of claim 13, wherein said additives are lipophilic or hydrophilic.

15. The process of claim 13, wherein said additives are incorporated into an oil phase of said liposome if lipophilic.

16. The process of claim 13, wherein said additives are added to the liquid phase after formation of the liposomes or in the case of liposomal desiccated powders added to the granulation phase.

17. The process of claim 1, wherein said temperature is room temperature.

18. The process of claim 17, wherein said drying is also in a heat which is less than 45 degrees Celsius.

19. The process of claim 18, wherein said moisture content is less than or equal to 3%.

20. The process of claim 1, wherein said encapsulated active compounds are one of:
   a) pharmaceutical drugs
   b) glycosides
   c) inclusion complexes with cyclodextrins,
   d) cannabinoids,
   e) derivatives of cannabinoids,
   f) nanocomplexed with lipids,
   g) nutraceutical compounds, and
   h) salts of nutraceutical components.

21. The process of claim 1, wherein said liposomes comprise from 0.01 to 0.1% Polysorbate 80 or Polysorbate 20 as stabilizers.

22. The process of claim 1, wherein before said step of adding said liposome in a formulation suspended in a water based solvent to a dried substrate, first forming an oil based fluid to dissolve lipophilic actives and lipophilic penetration enhancers, said lipophilic actives selected from one of pharmaceutical drugs, cannabinoids, terpenes, or nutraceutucals.

23. The process of claim 22, wherein said oil based fluid is added to a water based fluid and stirred at between approximately 500 and 2000 rpm modifying a surface tension so that large multilamellar liposomes are formed.

24. The process of claim 23, wherein said phospholipids are chosen from natural or synthetic phospholipids.

25. The process of claim 23, wherein said formulation is applied to a dry substrate to form a desiccated powder at or below 45 degrees Celsius.

26. The process of claim 22, wherein said liposomal fluid, after formation, is applied to a hydrocolloid substrate.

27. The process of claim 1, wherein said liposomes or said liposome formulation is formulated into one of a chewable gum, lozenge, wafer, granule, and thin orodispersible films.

* * * * *